United States Patent
Koch

(10) Patent No.: US 11,589,975 B1
(45) Date of Patent: Feb. 28, 2023

(54) SMALL DIAMETER VASCULAR PROSTHESIS

(71) Applicant: Bipore Medical Devices, Inc., Norwood, NJ (US)

(72) Inventor: Durmus Koch, Englewood, NJ (US)

(73) Assignee: Bipore Medical Devices, Inc., Norwood, NJ (US)

( * ) Notice: Subject to any disclaimer, the term of this patent is extended or adjusted under 35 U.S.C. 154(b) by 0 days.

(21) Appl. No.: 17/460,429

(22) Filed: Aug. 30, 2021

(51) Int. Cl.
*A61F 2/06* (2013.01)
*A61L 27/06* (2006.01)
*A61L 27/18* (2006.01)

(52) U.S. Cl.
CPC .............. *A61F 2/06* (2013.01); *A61L 27/06* (2013.01); *A61L 27/18* (2013.01); *A61F 2210/0071* (2013.01); *A61F 2230/0091* (2013.01)

(58) Field of Classification Search
CPC .............. A61F 2/06; A61F 2002/047; A61F 2210/0071; A61F 2/88; A61F 2/07; A61F 2230/0091; A61F 2220/005; A61F 2/0077
USPC .............................. 623/1.28, 1.32
See application file for complete search history.

(56) References Cited

U.S. PATENT DOCUMENTS

| | | | |
|---|---|---|---|
| 3,853,462 A | 12/1974 | Smith | |
| 4,760,849 A * | 8/1988 | Kropf | A61F 2/88 606/191 |
| 5,298,276 A * | 3/1994 | Jayaraman | A61F 2/06 427/2.25 |
| 6,156,064 A | 12/2000 | Chouinard | |
| 6,364,904 B1 * | 4/2002 | Smith | A61F 2/07 623/1.13 |
| 6,699,276 B2 | 3/2004 | Sogard et al. | |
| 7,828,833 B2 | 11/2010 | Haverkost et al. | |
| 9,107,741 B2 * | 8/2015 | Bui | A61F 2/07 623/1.13 |
| 10,869,749 B2 | 12/2020 | Spindler | |
| 10,888,412 B1 | 1/2021 | Koch | |
| 2003/0028245 A1 * | 2/2003 | Barclay | A61F 2/88 623/1.22 |
| 2005/0131515 A1 * | 6/2005 | Cully | A61F 2/07 623/1.13 |
| 2005/0137677 A1 | 6/2005 | Rush | |
| 2005/0288767 A1 | 12/2005 | Kujawski et al. | |
| 2006/0118236 A1 * | 6/2006 | House | A61L 27/16 623/1.39 |
| 2013/0184808 A1 * | 7/2013 | Hall | A61F 2/06 623/1.22 |
| 2013/0306232 A1 * | 11/2013 | Hedberg | A61F 2/07 156/250 |
| 2014/0135898 A1 | 5/2014 | Wagner et al. | |
| 2018/0303597 A1 * | 10/2018 | Spindler | A61F 2/07 623/1.13 |

* cited by examiner

*Primary Examiner* — Brian E Pellegrino
(74) *Attorney, Agent, or Firm* — Hoffmann & Baron, LLP

(57) ABSTRACT

A small diameter vascular prosthesis includes an outer textile graft, an intermediate self-supporting coil or stent and an inner microporous layer. The outer textile graft allows for tissue ingrowth. The inner microporous layer provides blood impermeability without preclotting the prosthesis. The coil or stent provides kink resistance and resistance again collapsing of the outer textile graft and the inner microporous layer.

19 Claims, 3 Drawing Sheets

SMALL DIAMETER VASCULAR PROSTHESIS

FIELD OF THE INVENTION

The present invention is related to a vascular prosthesis useful as a lumen or synthetic artery. The vascular prosthesis may be implanted via a surgical procedure to replace a part of a damaged blood vessel or to form a part of an anastomosis. In particular, it is useful as a small diameter vascular prosthesis having an outer diameter, for example, about 6 mm or less.

BACKGROUND OF THE INVENTION

Small diameter vascular grafts typically have poor resistance to collapsing and poor kink resistance. Further, typical small diameter prostheses typically require preclotting, for example with collagen, prior to use.

Stent-grafts have been used in large diameter vessels. In small diameter, non-vascular vessels, such as in the brain, ePTFE stent-grafts have been proposed. Such stent-grafts however do not general provide for tissue ingrowth on the exterior surfaces of the stent-grafts.

As such, there is a need in the art for a small diameter vascular prosthesis that allows tissue ingrowth about its exterior, has kink resistance, has resistance against collapse, and is blood tight without the need for preclotting.

SUMMARY OF THE INVENTION

In one aspect of the present invention, a vascular prosthesis includes a tubular graft comprising a tubular textile wall having biocompatible yarns in a textile construction, the wall having an inner surface and an opposed outer surface; a self-supporting metallic coil secured about at least a portion of the inner surface of the tubular textile wall, the metallic coil having interstices; and a microporous layer securably disposed over at least a portion the metallic coil and portions of the inner surface of the tubular textile wall proximal to the interstices of the metallic coil to provide a fluid tight implantable prosthesis. The textile wall allows for tissue ingrowth after implantation. The microporous layer prevents clotting and provides for fluid or blood tightness without preclotting with, for example, collagen. The metallic coil prevents kinking and collapsing of the vascular prosthesis.

The prosthesis may include biocompatible yarns, including synthetic biocompatible materials such as polyesters, polypropylenes, polyethylenes, polyurethanes, polytetrafluoroethylenes, and combinations thereof. The biocompatible yarns may be monofilament yarns or multifilament yarns. Desirably, the biocompatible yarns are polyethylene terephthalate yarns. Useful textile constructions include woven, knitted, and/or braided textile constructions.

The tubular textile wall may be a crimped textile wall or a non-crimped textile wall.

The prosthesis may have an outer diameter of about 6 mm or less that about 6 mm, for example, from about 2 mm to about 5 mm.

The prosthesis may have a wall thickness of about 250 micrometers or less than 250 micrometers (about 0.010 inches or about 10 mil).

The metallic coil may be a helically wound metallic wire. The metallic coil may be a helically wound, planar ribbon. The planar ribbon may have a thickness from about 50 micrometers (about 0.002 inches or about 2 mil) to about 75 micrometers (about 0.003 inches or about 3 mil). The metallic coil includes any useful biocompatible metallic material, for example stainless steel, nickel titanium alloy (e.g., NITINOL), cobalt-based alloy (e.g., ELGILOY), platinum, gold, titanium, tantalum, niobium and combinations thereof.

The microporous layer may include polytetrafluoroethylene (PTFE) or expanded polytetrafluoroethylene (ePTFE). The microporous layer may have a thickness from about 50 micrometers (about 0.002 inches or about 2 mil) to about 75 micrometers (about 0.003 inches or about 3 mil).

The prosthesis is a fluid tight implantable prosthesis, for example configured to obviate the leaking of blood at a blood pressure of up to approximately 300 mmHg. The fluid tight implantable prosthesis may have a water permeability of about 0.16 ml/min/cm$^2$ at 120 mm Hg pressure or less than 0.16 ml/min/cm$^2$ at 120 mm Hg pressure.

The prosthesis may further include a thermoplastic elastomer disposed over at least a portion the metallic coil and portions of the tubular textile wall and the microporous layer proximal to the interstices of the metallic coil. The thermoplastic elastomer may be polyether block amide (PEBAX) or polyethylene (PE). The prosthesis is free sutures, staples or pins for securing the tubular textile wall, the metallic coil, and the microporous layer to one and another.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

DETAILED DESCRIPTION OF THE INVENTION

The present invention is directed towards a small diameter vascular prosthesis. The outer diameter of the vascular prosthesis 10 of the present invention, as depicted as an outer diameter (D) in FIG. 2, may be about 6 mm or less. The vascular prosthesis 10 of the present inventions provides for tissue ingrown after implantation. Further, the vascular prosthesis 10 is fluid or blood tight without the need for preclotting, for example by preclotting with collagen. Moreover, the vascular prosthesis 10 is self-supporting and kink resistant. These and further attributes are described below.

While the present invention is particularly useful for small diameter vascular prostheses, the present invention is not so limited. For example, the vascular prosthesis 10 of the present invention may suitably be used for a medium diameter vascular grafts (e.g., having an outer diameter of about 6 mm to about 8 mm) or even for large diameter vascular grafts (e.g., having a diameter greater than 8 mm). The vascular graft 10 may have an outer diameter from about 6 mm to about 20 mm, including from about 10 mm to about 15 mm.

Figure 1:
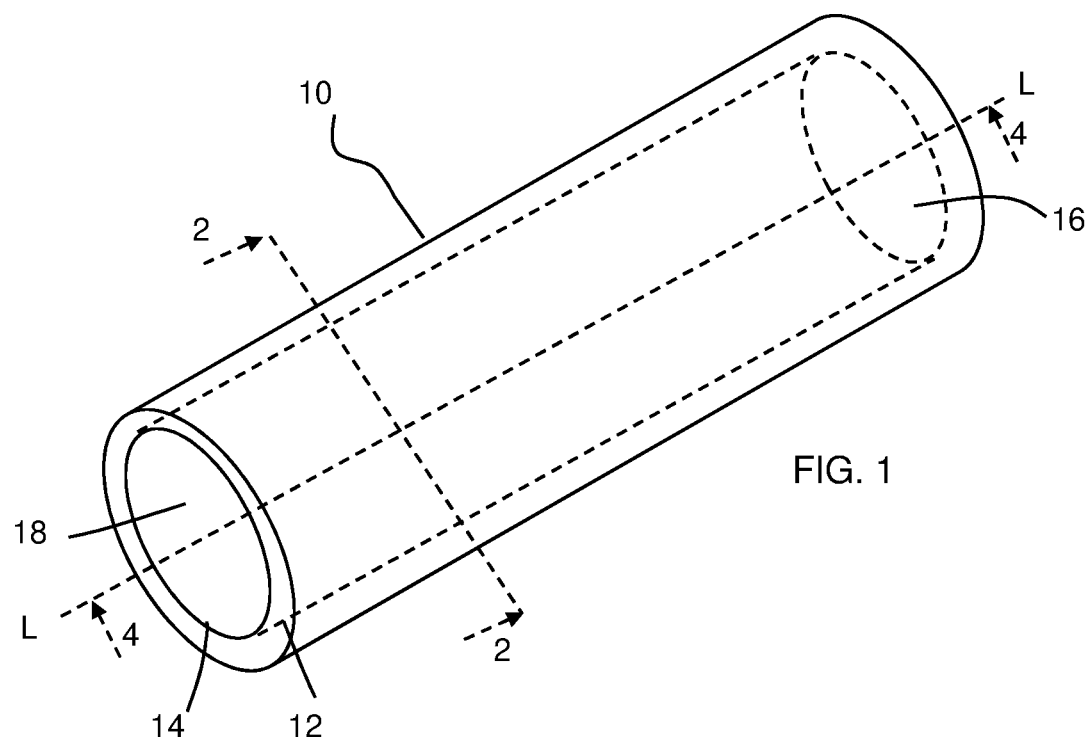
FIG. 1 is a perspective view of the vascular prosthesis of the present invention.

In further detail, FIG. 1 depicts the vascular prosthesis 10 of the present invention. Vascular prosthesis 10 is a hollow tubular member having a prosthesis tubular wall 12 along a longitudinal axis (L) and opposed open ends 14, 16. The vascular prosthesis 10 is provided with an open lumen 18 to serve as a conduit for fluid flow, such as blood flow. While the vascular prosthesis 10 is depicted as being a cylinder having a straight wall, the present invention is not so limited. The vascular prosthesis 10 of the present invention may have portions of its wall 12 being flared, curved, or the like. Further, while the vascular prosthesis 10 is depicted as having opposed single open ends 14, 16, the present invention is not so limited. One or both ends 14, 16 have one or more open ends. For example, one end of the vascular prosthesis 10 may be bifurcated (not shown).

Figure 2:
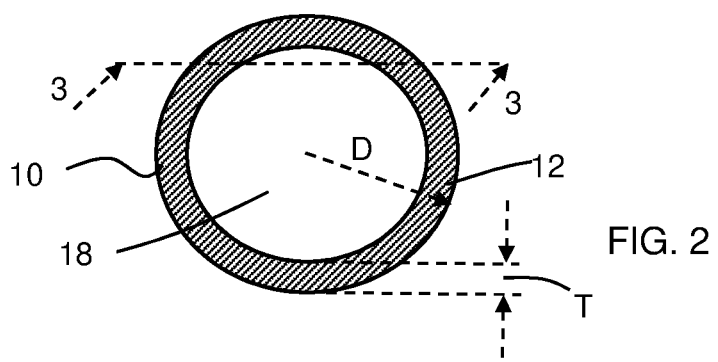
FIG. 2 is a cross-sectional view of the vascular prosthesis of FIG. 1 taken along the 2-2 axis.

FIG. 2 depicts a cross-sectional view of the vascular prosthesis 10 of FIG. 1 taken along the 2-2 axis in FIG. 1. The cross-sectional view depicts the open lumen 18 of the vascular prosthesis 10. The wall 12 is depicted as a single cross-hatched structure in FIG. 2 merely for the sake of simplicity. The vascular prosthesis 10 may have an outer diameter (D) about 6 mm or less. Useful outer diameters include from about 1 mm to about 6 mm, desirable from about 2 mm to about 5 mm, more desirably from about 3 mm to about 4 mm. Further, the wall 12 may have a thickness (T) of about 250 micrometers or less than 250 micrometers (about 0.010 inches or about 10 mil). Useful wall thicknesses (T) include from about 200 micrometers (about 0.008 inches or about 8 mil) to about 250 micrometers (about 0.010 inches or about 10 mil), including from about 200 micrometers (about 0.008 inches or about 8 mil) to about 230 micrometers (about 0.009 inches or about 9 mil).

The components of the tubular wall 12 are depicted in further detail as described below.

Figure 3:
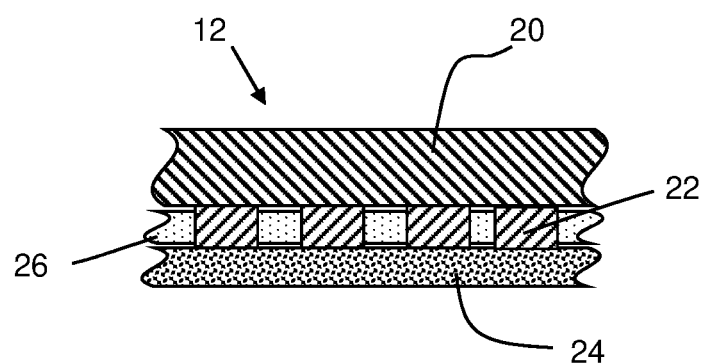
FIG. 3 is a cross-sectional view of a portion of the wall of the vascular prosthesis of FIG. 2 taken along the 3-3 axis.

FIG. 3 is a partial cross-sectional view of the prosthesis wall 12 of FIG. 2 taken along the 3-3 axis in FIG. 2. The prosthesis wall 12 incudes an outer textile layer 20 and an inner microporous layer 24. A stent or coil 22 is securably disposed between the outer textile layer 20 and the inner microporous layer 24. A thermoplastic elastomer 26 may optionally be disposed within the wall 12 to aid in the securement of the coil 22 to the microporous layer 24 and/or to the outer textile layer 20.

The outer textile layer 20 of the prosthesis wall 12 or portions of prosthesis wall 12 of the present invention may include wall portions made from any biocompatible, durable material, including, for example polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. As used herein, textile materials are filaments or yarns that are woven, braided, knitted, filament-spun, and the like to form textile graft material. Desirably, the outer textile layer 20 of the present invention is a woven poly(ethylene terephthalate) or woven PET textile tubular member.

The yarns may be of the monofilament, multifilament, or spun type. The yarns may have a linear density from about 18 denier (about 20 decitex) to about 140 denier (about 154 decitex). The yarns may be flat, twisted, and/or textured, and may have high, low or moderate shrinkage and/or bulk and crimp properties. Twisted yarns include S-twisted yarns and Z-twisted yarns.

The outer textile layer 20 of the present invention may be woven from yarns using any known weave pattern, including simple plain weaves, basket weaves, twill weaves, velour weaves and the like. Weave patterns include warp yarns running along the longitudinal length of the woven product and weft also known as fill yarns running around the width or circumference of the woven product. The warp and the fill yarns are at approximately 90 degrees to one another with fabric flowing from the machine in the warp direction.

Knitting involves the interlooping or stitching of yarn into vertical columns (wales) and horizontal rows (courses) of loops to form the knitted fabric structure. In warp knitting, the loops are formed along the textile length, i.e., in the wale or warp direction of the textile. Useful knitting patterns include, but are not limited to, locknit knits (also referred to as tricot or jersey knits), reverse locknit knits, sharkskin knits, queenscord knits, atlas knits, velour knits, and the like.

Desirably, with the use of textile wall constructions, the outer textile layer 20 permits tissue ingrowth after implantation.

The microporous layer 24 may include polytetrafluoroethylene (PTFE) or expanded polytetrafluoroethylene (ePTFE). The microporous layer 24 may have a non-limiting thickness from about 50 micrometers (0.002 inches or 2 mil) to about 75 micrometers (0.003 inches or 3 mil).

Expanded PTFE (ePTFE) tubes and films may be made by extrusion of PTFE resin, typically mixed with a lubricant. The microporous structure of ePTFE may be obtained by a process that involves rapid stretching of the extruded tube at high temperature. The ePTFE structure may be characterized by nodes, about 5-10 m wide by about 5-100 m long, interconnected by fibrils of less than about 0.5 m in diameter. The degree of porosity of an ePTFE graft is controlled by the distance between the nodes. In clinically used grafts this distance may be in of the order of about 30 m.

The microporous layer 24 may include microporous PTFE substantially free of the node and fibril structure associated with typical ePTFE. Such microporous PTFE may be made by calendering and stretching PTFE films. For vascular applications the average pore size may be less than about 20 m, including from about 1 m to about 5 m.

With the use of the microporous layer 24, the vascular prosthesis 10 may be a fluid tight implantable prosthesis which configured to obviate the leaking of blood at a blood pressure of up to approximately 300 mmHg. There is no need for preclotting with collagen or the like as the microporous layer 24 is generally blood impermeable. Such a fluid tight implantable prosthesis may have a water permeability of about 0.16 ml/min/cm$^2$ at 120 mm Hg pressure or less than 0.16 ml/min/cm$^2$ at 120 mm Hg pressure.

The use of the microporous layer 24 with the vascular prosthesis also offers other benefits. For example, PTFE and ePTFE layers also prevent or inhibit or minimize undesirable adhesion or build-up of materials, such as thrombus formation, platelet aggregation, and the like. Such benefits are especially advantageous in small diameter vascular prostheses.

The stent or coil 22 is desirably a metallic coil of a helically wound metallic wire. If desired, the stent or coil 22 may be laser cut, or the like, from a tubular frame. The wire may be round or flattened or flat, such as a planar ribbon. Desirably, the metallic coil 22 is a helically wound, planar ribbon. The planar ribbon may have a thickness from about 50 micrometers (about 0.002 inches or about 2 mil) to about 75 micrometers (about 0.003 inches or about 3 mil). The metallic coil 22 may include a metallic material, such as stainless steel, nickel titanium alloy (e.g., NITINOL), cobalt-based alloy (e.g., ELGILOY), platinum, gold, titanium, tantalum, niobium and combinations thereof. Desirably, the metallic coil 22 includes nickel titanium alloy (e.g., NITINOL).

Metallic materials for the stent or coil 22 are preferred as these materials provide strength against collapsing and kink resistance. The outer textile layer or graft 20 and/or the inner microporous layer or graft 24 may kink when bent if the stent or coil 22 is not present for support. Further, the outer textile layer or graft 20 and/or the inner microporous layer or graft 24 may collapse under minor applied force if the stent or coil 22 is not present for support. Polymeric materials may also be used for the stent or coil 22 where resistance against collapsing is less critical.

The prosthesis 10 may further include a thermoplastic elastomer disposed over at least a portion the metallic coil and portions of the tubular textile wall and the microporous layer proximal to the interstices of the metallic coil. Useful thermoplastic elastomers include polyether block amide (PEBAX) or polyethylene (PE). The elastomeric material may be applied over the microporous layer 24 and/or over the coil 22. The outer textile layer 20 may then be disposed over the coil 22.

Figure 4:
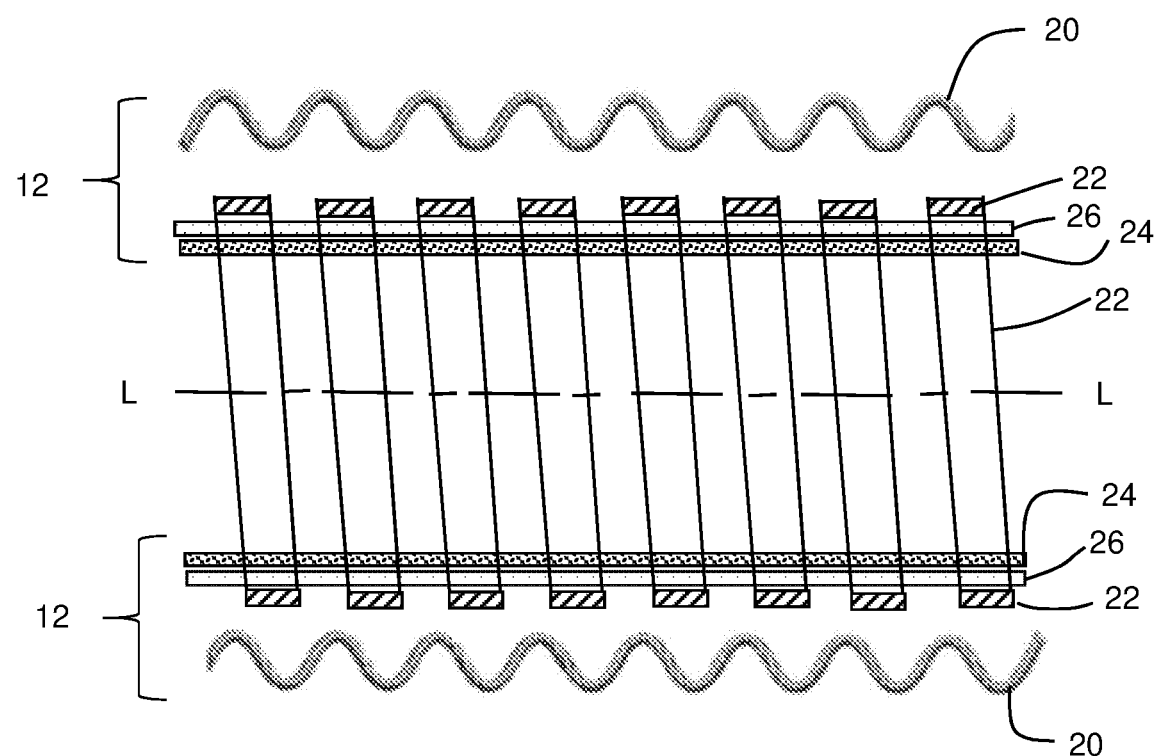
FIG. 4 depicts the components of the vascular prosthesis of FIG. 1 taken along the 4-4 axis prior to their securement in forming the vascular prosthesis of the present invention.

As depicted in FIG. 4, the outer textile layer 20 may be a crimped textile layer. Such a crimped textile layer is characterized by a series of peaks and valleys in the textile layer as shown. The outer textile layer may be crimped prior to its securement to the underlying coil 22 and microporous layer 24.

As depicted in FIG. 4, the outer textile layer 20 may be securably disposed over the stent or coil 22 and the inner microporous layer 24. A thermoplastic elastomer 26 may also be disposed over the microporous layer 24 and/or the coil 22. The outer textile layer 20 may be secured to the coil 22 and the microporous layer 24 through chemical shrinkage techniques. For example, the coil 22 and the microporous layer 24 may be disposed on a mandrel (not shown). The crimped outer textile layer 20 may then be disposed over the mandrel and over the coil 22 and microporous layer 24 arrangement. The crimped the outer textile layer 20 then be secured the coil 22 and microporous layer 24 arrangement through chemical shrinkage techniques. Such chemical shrinkage techniques may include the use of methyl chloride at elevated temperatures, such as from about 200° F. (about 93° C.) to about 250° F. (about 121° C.) for moderate periods of time, for example from 45 minutes to 60 minutes.

Figure 5:
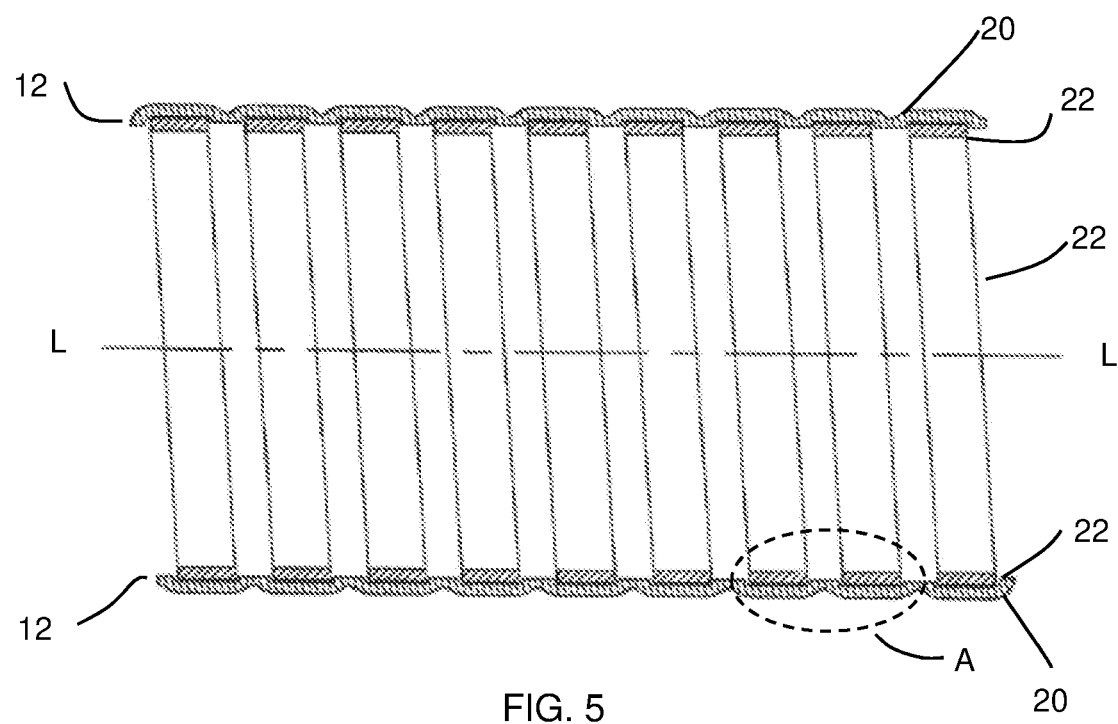
FIG. 5 depicts the components of the vascular prosthesis of FIG. 4 secured together to form the vascular prosthesis of the present invention.

The so produced vascular prosthesis 10 is depicted in FIG. 5. The outer textile layer 20 is securably disposed over the coil 22 and microporous layer 24 arrangement to provide a blood impermeably, kink resistant and self-supporting vascular prosthesis. While the coil 22 is depicted a as being disposed within the peaks of the crimped outer textile layer 20, the present invention is not so limited. The coil 22 may be disposed along any of the portion of the outer textile layer 20, including peaks, valleys, and combinations thereof.

Figure 5A:
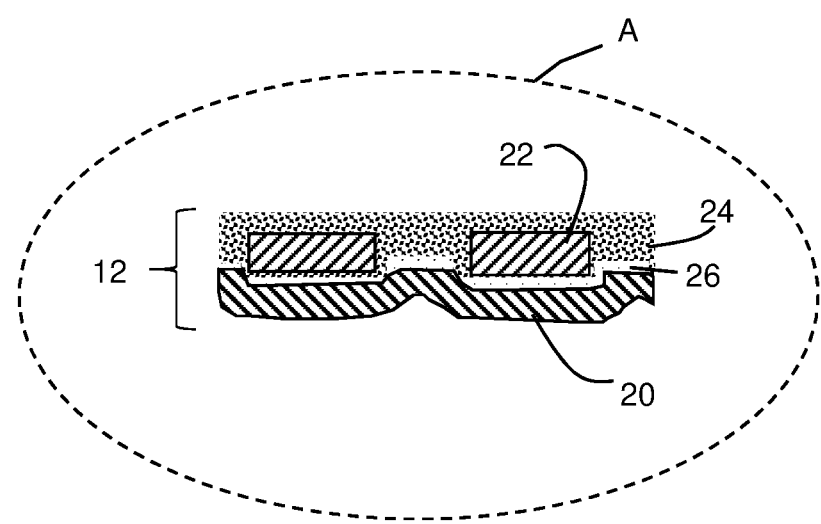
FIG. 5A is an exploded view of a portion (A) of the vascular prosthesis of FIG. 5.

FIG. 5A is an exploded view of a portion "A" of the tubular wall 12 of the vascular prosthesis 10. As depicted in FIG. 5A the thermoplastic elastomer 26 is useful in securing the outer textile layer 20, the coil 22, and the microporous layer 24 to each other, thereby forming, as least functionally, a unitary tubular wall.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

What is claimed is:

1. A vascular prosthesis comprising:
   a tubular graft comprising a tubular textile wall having a plurality of crimps defined by a plurality of helical peaks and valleys and having biocompatible yarns in a textile construction, the wall having an inner surface and an opposed outer surface;
   a self-supporting, collapsing-resistant metallic coil of a helically wound metallic wire having an inner portion and an opposed outer portion, the outer portion of the metallic coil being disposed and juxtaposingly and directly secured to at least a portion of the inner surface of the tubular textile wall, the metallic coil having interstices; and
   a microporous layer securably disposed about the inner portion of the metallic coil and juxtaposingly and directly secured at portions of the inner surface of the tubular textile wall proximal to the interstices of the metallic coil to provide a fluid tight implantable prosthesis.

2. The prosthesis of claim 1, wherein the biocompatible yarns are selected from the group consisting of polyesters, polypropylenes, polyethylenes, polyurethanes, polytetrafluoroethylenes, and combinations thereof.

3. The prosthesis of claim 1, wherein the biocompatible yarns are monofilament yarns or multifilament yarns.

4. The prosthesis of claim 1, wherein the biocompatible yarns are polyethylene terephthalate yarns.

5. The prosthesis of claim 1, wherein the textile construction is a woven, knitted, or braided textile construction.

6. The prosthesis of claim 1, wherein the prosthesis has an outer diameter of about 6 mm or less than 6 mm.

7. The prosthesis of claim 6, wherein the outer diameter is from about 2 mm to about 5 mm.

8. The prosthesis of claim 1, wherein the prosthesis has a wall thickness of about 250 micrometers or less than 250 micrometers (0.010 inches, or 10 mil).

9. The prosthesis of claim 1, wherein the metallic wire is a planar ribbon.

10. The prosthesis of claim 9, wherein the planar ribbon has a thickness from about 50 micrometers (0.002 inches or 2 mil) to about 75 micrometers (0.003 inches or 3 mil).

11. The prosthesis of claim 1, wherein the metallic coil comprises a metallic material selected from the group consisting of from stainless steel, nickel titanium alloy, cobalt-based alloy, platinum, gold, titanium, tantalum, niobium and combinations thereof.

12. The prosthesis of claim 1, wherein the metallic coil comprises nickel titanium alloy.

13. The prosthesis of claim 1, wherein the microporous layer comprises polytetrafluoroethylene or expanded polytetrafluoroethylene.

14. The prosthesis of claim 13, wherein the microporous layer has a thickness from about 50 micrometers to about 75 micrometers.

15. The prosthesis of claim 1, the fluid tight implantable prosthesis is configured to obviate the leaking of blood at a blood pressure of up to approximately 300 mmHg.

16. The prosthesis of claim 1, the fluid tight implantable prosthesis has a water permeability of about 0.16 ml/min/cm$^2$ at 120 mm Hg pressure or less than 0.16 ml/min/cm$^2$ at 120 mm Hg pressure.

17. A vascular prosthesis consisting of:
a tubular graft comprising a tubular textile wall having a plurality of crimps defined by a plurality of helical peaks and valleys and having biocompatible yarns in a textile construction, the wall having an inner surface and an opposed outer surface;
a self-supporting, non-collapsing metallic coil of a helically wound metallic wire having an inner portion and an opposed outer portion, the outer portion of the metallic coil being disposed and juxtaposingly and directly secured to at least a portion of the inner surface of the tubular textile wall, the metallic coil having interstices;
a microporous layer securably disposed about the inner portion of the metallic coil; and
a thermoplastic elastomer disposed over a portion of the microporous layer and underneath a portion of the inner portion of the metallic coil to secure said portion of metallic coil to said inner portion of the metallic coil;
wherein other portions of the microporous layer proximal to the interstices of the metallic coil and distal from the thermoplastic elastomer are disposed at and secured to portions of the inner surface of the tubular textile wall threat to provide a fluid tight implantable prosthesis.

18. The prosthesis of claim 17, wherein the thermoplastic elastomer is polyether block amide or polyethylene.

19. A vascular prosthesis consisting essentially of:
a tubular graft comprising a tubular textile wall having a plurality of crimps defined by a plurality of helical peaks and valleys and having biocompatible yarns in a textile construction, the wall having an inner surface and an opposed outer surface;
a self-supporting, non-collapsing metallic coil of a helically wound, planar ribbon having an inner portion and an opposed outer portion, the outer portion of the metallic coil being disposed and juxtaposingly secured to at least a portion of the inner surface of the tubular textile wall, the metallic coil having interstices; and
a microporous layer securably disposed about the inner portion the metallic coil and having portions disposed at portions of the inner surface of the tubular textile wall proximal to the interstices of the metallic coil;
wherein said portions of the microporous layer are juxtaposingly and directly secured to said portions of the inner surface of the textile tubular wall to provide a fluid tight implantable prosthesis;
and
wherein the microporous layer comprises polytetrafluoroethylene or expanded polytetrafluoroethylene.

* * * * *